United States Patent
McCleary et al.

(10) Patent No.: US 7,585,329 B2
(45) Date of Patent: Sep. 8, 2009

(54) MODULAR PROXIMAL BODY TRIAL

(75) Inventors: Larry McCleary, Warsaw, IN (US);
Jonathan Carr, Warsaw, IN (US); Joel Rhoades, Pierceton, IN (US); David Daniels, Winona Lake, IN (US)

(73) Assignee: DePuy Products, Inc., Warsaw, IN (US)

( * ) Notice: Subject to any disclaimer, the term of this patent is extended or adjusted under 35 U.S.C. 154(b) by 4 days.

(21) Appl. No.: 11/605,099

(22) Filed: Nov. 28, 2006

(65) Prior Publication Data
US 2008/0125867 A1    May 29, 2008

(51) Int. Cl.
*A61F 2/36* (2006.01)
(52) U.S. Cl. .................. 623/23.15; 623/23.47
(58) Field of Classification Search ......... 623/22.4, 623/22.41, 22.42, 22.46, 23.15, 23.44–23.47, 623/20.15, 23.18, 23.21, 23.22
See application file for complete search history.

(56) References Cited

U.S. PATENT DOCUMENTS

| | | | |
|---|---|---|---|
| 5,876,459 A | 3/1999 | Powell | |
| 5,906,644 A | 5/1999 | Powell et al. | |
| 6,090,146 A * | 7/2000 | Rozow et al. | 623/22.42 |
| 6,193,759 B1 | 2/2001 | Ro et al. | |
| 6,692,530 B2 | 2/2004 | Doubler et al. | |
| 2003/0093080 A1 | 5/2003 | Brown et al. | |
| 2003/0204269 A1 * | 10/2003 | Gerbec et al. | 623/23.47 |
| 2004/0054419 A1 | 3/2004 | Serra et al. | |
| 2004/0064186 A1 | 4/2004 | McCleary et al. | |
| 2004/0122437 A1 | 6/2004 | Dwyer et al. | |
| 2004/0122440 A1 | 6/2004 | Daniels et al. | |
| 2004/0122525 A1 | 6/2004 | Daniels et al. | |
| 2004/0267266 A1 | 12/2004 | Daniels et al. | |
| 2004/0267267 A1 | 12/2004 | Daniels et al. | |
| 2004/0267372 A1 | 12/2004 | Vanasse et al. | |
| 2005/0004679 A1 | 1/2005 | Sederholm et al. | |

FOREIGN PATENT DOCUMENTS

| | | |
|---|---|---|
| EP | 1 493 407 | 1/2005 |
| WO | WO 03/094803 | 11/2003 |

* cited by examiner

*Primary Examiner*—Corrine M McDermott
*Assistant Examiner*—Megan Wolf
(74) *Attorney, Agent, or Firm*—Maginot, Moore & Beck

(57) ABSTRACT

A system and method for trialing a modular hip replacement system permits evaluation and replication of the anatomic anteversion rotational angle of the femur. In one embodiment, a femoral hip implant kit includes at least one distal implant and a plurality of femoral heads, each of the plurality of femoral heads having a diameter different from the diameter of the other of the plurality of femoral heads. The kit includes a proximal trial housing with a bore within the housing, the bore configured to receive a portion of the distal implant, a collet located within the bore, the collet including an outer wall portion extending between a top surface portion and a bottom surface portion, a collapsing member for engaging the portion of the distal implant and for forcing the top surface portion of the collet toward the bottom surface portion of the collet along a first axis.

11 Claims, 6 Drawing Sheets

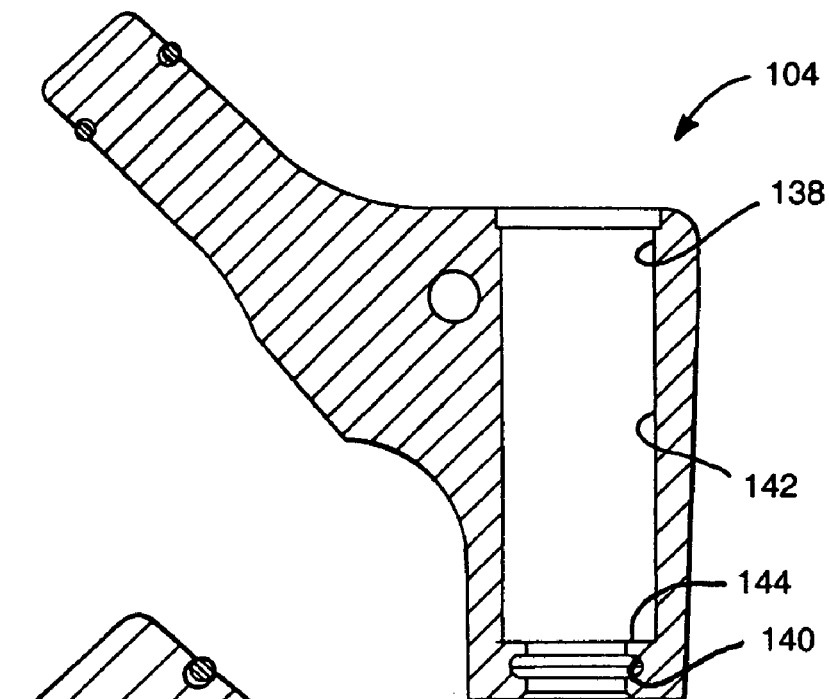
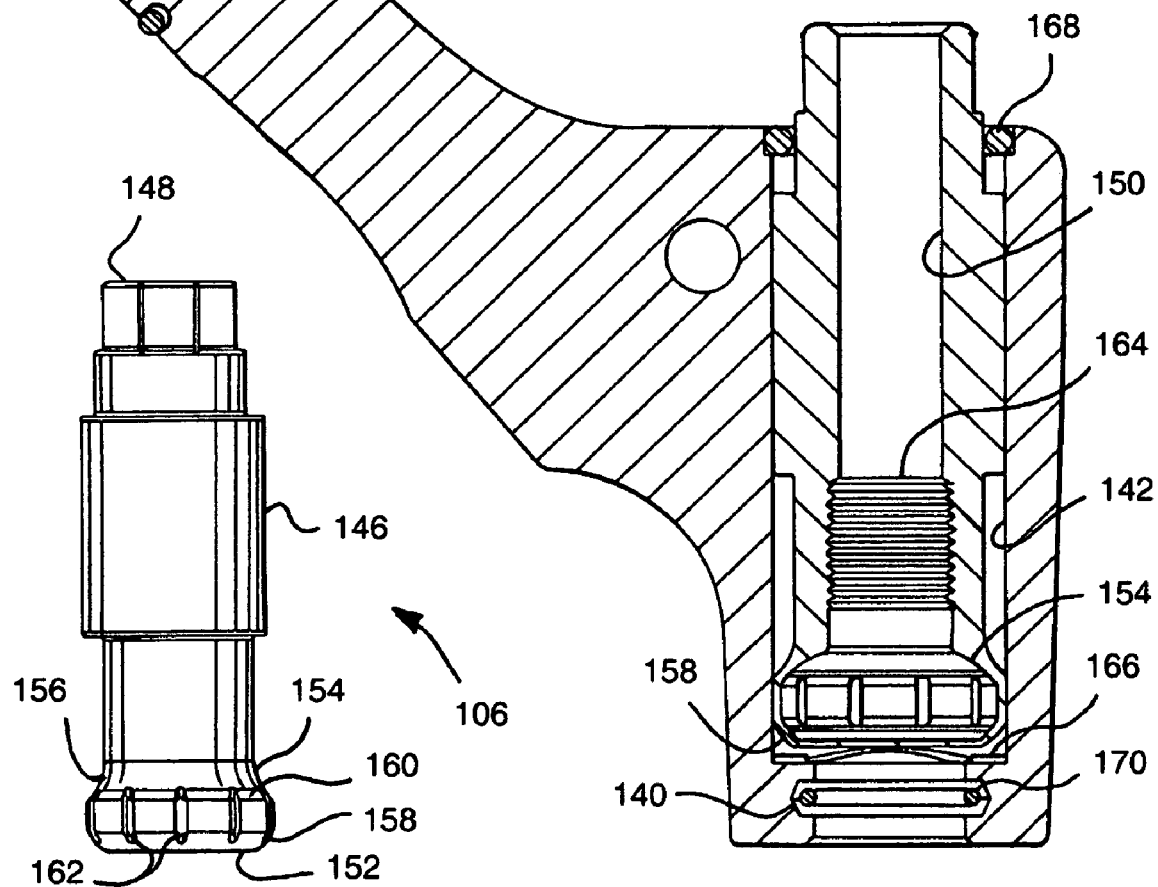
FIG. 3
FIG. 4
FIG. 5

MODULAR PROXIMAL BODY TRIAL

FIELD OF THE INVENTION

This invention relates to orthopedic appliances and, more particularly, to a system and method capable of gauging the degree of anteversion of the femur.

BACKGROUND

During the lifetime of a patient, it may be necessary to perform a joint replacement procedure on the patient as a result of, for example, disease or trauma. The joint replacement procedure, or joint arthroplasty, may involve the use of a prosthesis which is implanted into one of the patient's bones. In the case of a hip replacement procedure, a femoral prosthesis is implanted into the patient's thigh bone or femur. One type of early femoral prosthesis was typically constructed as a one-piece structure having an upper portion which includes a spherically-shaped head which bears against the patient's pelvis or acetabulum, along with an elongated intramedullary stem which is utilized to secure the femoral component to the patient's femur. In order to secure the prosthesis to the patient's femur, the medullary canal of the patient's femur is first surgically prepared (e.g. reamed and/or broached) such that the intramedullary stem of the femoral prosthesis may be subsequently implanted therein. The femoral prosthesis may be press fit into the medullary canal or, in the alternative, bone cement may be utilized to secure the femoral prosthesis within the medullary canal.

During performance of a joint replacement procedure, it is generally important to provide the orthopaedic surgeon with a certain degree of flexibility in the selection of a prosthetic device. In particular, the anatomy of the bone into which the prosthesis is to be implanted may vary somewhat from patient to patient. For example, in the case of a femoral prosthesis, the patient's femur may be relatively long or relatively short thereby requiring use of a femoral prosthesis which includes a stem that is relatively long or short, respectively. Moreover, in certain cases, such as when use of a relatively long stem length is required, the stem must also be bowed in order to conform to the anatomy of the patient's femur.

Such a need for prostheses of varying shapes and sizes can create a number of problems in regard to use of a one-piece prosthesis. For example, a hospital or surgery center must maintain a relatively large inventory of prostheses in order to have the requisite mix of prostheses needed for certain situations such as trauma situations and revision surgery. Moreover, since the bow of the stem must conform to the bow of the intramedullary canal of the patient's femur, rotational positioning of the upper portion (i.e. proximal end) of the prosthesis is limited thereby rendering precise locating of the upper portion and hence the head of the prosthesis very difficult. In addition, since corresponding bones of the left and right side of a patient's anatomy (e.g. left and right femur) may bow in opposite directions, it is necessary to produce "left" and "right" variations of the prosthesis in order to provide proper anteversion of the bowed stem thereby further increasing the inventory of prostheses which must be maintained.

As a result of these and other drawbacks, a number of modular prostheses have been designed. As its name implies, a modular prosthesis is constructed in modular form so that the individual elements or features of the prosthesis can be selected to fit the needs of a given patient's anatomy. For example, modular prostheses have been designed which include a proximal neck component which can be assembled to any one of numerous distal stem components in order to create an assembly which fits the needs of a given patient's anatomy. Such a design allows the distal stem component to be selected and thereafter implanted in the patient's bone in a position which conforms to the patient's anatomy while also allowing for a limited degree of independent positioning of the proximal neck component relative to the patient's pelvis.

In another type of modular implant, three components (in addition to the head) are utilized: a distal stem component that is engaged within the femur, a proximal metaphyseal filling component, and an intermediate neck component that supports the head component on the distal stem component. The provision of three components has greatly increased the degree of flexibility in producing a total hip implant that most closely approximates the patient's skeletal anatomy and normal joint movement. One such system is the S-ROM® total hip system marketed by DePuy Orthopaedics, Inc. The S-ROM® total hip system offers neck and head components having different lengths, different lateral offsets of the neck relative to the stem, as well as different stem configurations.

In order to properly size the final implant, many systems utilize trial implants, commonly referred to as simply trials. Thus, in modular systems such as the S-ROM® instrument system, neck trials, proximal body trials, distal stem trials, head trials and sleeve trials can be provided. Each trial is provided in a number of sizes and geometries to give the surgeon a wide range of combination from which to choose. The trials afford the orthopaedic surgeon the opportunity to assess the fit and position of a final implant without having to complete the fixation. Like the implant systems itself, the trials are modular to reduce the inventory of components and the complexity of the trialing process.

Success of the hip replacement procedure depends in large part on the technical precision with which the final implant is inserted and the modular components oriented relative to each other. Current trialing systems have performed well in assessing implant size and gross orientation, relying primarily on laser marking, for example. There remains, however, an unfulfilled need for a trialing system (as well as a modular implant system) that is able to more accurately reproduce the anteversion angle of the femur. The anteversion angle is an angle of rotation between the ball end of the femur and the plane of the intramedullary canal of the bone. In the context of the modular implant, the anteversion angle is the relative angular rotation of the proximal neck component relative to the distal stem component. Proper rotational position, or anteversion angle, allows for accurate and stable reproduction of the mechanical orientation and function of the reconstructed hip joint.

For implants having a straight distal stem, the proper anteversion angle can be obtained by simply spinning the distal stem within the prepared bore in the femur. In a typical case, the surgeon can visually evaluate the orientation of the proximal body relative to the surrounding anatomy. If a trial is used, the trial is removed and the final prosthesis is implanted as close to the trial position as possible. Sometimes, x-rays are used to verify the rotational alignment, while some systems rely upon external references to verify alignment.

The S-ROM® total hip system described above utilizes laser markings on the proximal end of the distal stem and on the proximal sleeve. These markings enable the surgeon to measure relative anteversion rotational alignment between the components. Since the sleeve has infinite anteversion it is not necessarily oriented relative to a bony landmark that can be used to define the anteversion angle. In fact, for simplicity, most current sleeves are oriented with the laser marking pointing directly laterally into the remaining available bone of the femur.

The problem of ensuring proper anteversion alignment is exacerbated where the modular system includes a curved distal stem. As explained above, where a long distal stem is utilized, it must be curved to follow the natural shape of the femur. Obviously, the rotational alignment of a curved stem cannot be modified once the curved stem is implanted.

In accordance with some prior art modular systems, the anteversion is determined by using a variety of trial femoral heads which allow a surgeon to vary the position of the head center along the axis of the neck thereby altering the head offset in both the horizontal and vertical directions simultaneously. Other systems provide a combination of trial femoral heads with two or three trial neck components that allow pure horizontal variability. Some systems even offer independent horizontal and vertical control in addition to the effects of the trial heads.

More recently, an additional degree of freedom has been provided by allowing modifications to the anteversion angle about the axis of the stem. A trialing system of this type, with four independent degrees of freedom (i.e., translation along the neck axis, horizontal offset, vertical offset, and anteversion angle), gives the surgeon tremendous flexibility in positioning the head center, thus providing an improved opportunity for optimization of the joint biomechanics.

While the foregoing systems are useful, they suffer from various limitations. For example, the anteversion angle in known systems can be changed in either discrete, indexable jumps (e.g., 10 degree increments) or with infinitely fine, continuous movement. The precision of systems using discrete jumps is limited by the size of the jump. This presents a limitation in that even rotational changes on the order of about 5 degrees can appreciably affect impingement, dislocation rate, and the range of motion of a joint.

The systems that provide infinitely fine, continuous movement overcome the limitation of using discrete angles. The continuous movement systems, however, are also limited. Specifically, once the configuration of the trial has been established, it is necessary to perform a trial reduction of the joint to verify that the optimum configuration has been achieved. Prior art continuous movement systems, however, do not provide a sufficiently strong coupling between the trial and the distal body. Accordingly, the continuous movement systems frequently fail to hold rotational stability during the trial reduction. This requires the anteversion to be re-established and another trial reduction performed, prolonging the surgical procedure.

What is needed is a system which allows a proximal trial to be attached to a distal body with a full 360 degree freedom of rotation and which provides for sufficient stability to resist trial failure. A further need exists for a system that may be used with a distal body that is one or more of a broach, a reamer, a trial and an implant.

SUMMARY

A system and method for trialing a modular hip replacement system permits evaluation and replication of the anatomic anteversion rotational angle of the femur. In one embodiment, a femoral hip implant kit includes at least one distal implant and a plurality of femoral heads, each of the plurality of femoral heads having a diameter different from the diameter of the other of the plurality of femoral heads. The kit includes a proximal trial housing with a bore within the housing, the bore configured to receive a portion of the distal implant, a collet located within the bore, the collet including an outer wall portion extending between a top surface portion and a bottom surface portion, a collapsing member for engaging the portion of the distal implant and for forcing the top surface portion of the collet toward the bottom surface portion of the collet along a first axis, thereby forcing the outer wall portion in a direction generally perpendicular to the first axis such that the outer wall portion is located outwardly of the top surface portion and the bottom surface portion with respect to the first axis.

In another embodiment, a femoral hip implant proximal trial includes an housing and a bore within the housing that is configured to receive a portion of a distal implant. A resiliently collapsible collet is located within the bore and a collapsing member engages the portion of the distal implant and is operable to resiliently collapse the collet within the bore such that the collet is resiliently pressed against the wall of the bore, so as to angularly lock the housing with the distal implant.

One method in accordance with the invention includes providing a bore within a proximal trial housing, receiving a portion of a distal implant within the bore, engaging the portion of the distal implant with a collapsing member, and moving an upper portion of the collet closer to a bottom portion of the collet along a first axis. The method includes forcing an outer wall portion of the collet in a direction generally perpendicular to the first axis in response to the moving of the upper portion of the collet; and contacting the wall of the bore with the outer wall portion of the collet such that the distal implant is angularly locked to the proximal trial housing.

BRIEF DESCRIPTION OF THE DRAWINGS

FIG. 3 depicts a side cross-section view of the proximal trial body of FIG. 1 with the distal trial stem and collet removed;

FIG. 4 depicts a side plan view of a collet that may be used with the proximal trial body of FIG. 1 in accordance with principles of the present invention;

FIG. 5 depicts a side cross-section view of the proximal trial body of FIG. 1 with the collet of FIG. 4 and a spring washer within a main bore portion and a spring within a cavity which extends outwardly from the bore is which is separated from the main bore portion by a lip;

DETAILED DESCRIPTION

Figure 1:
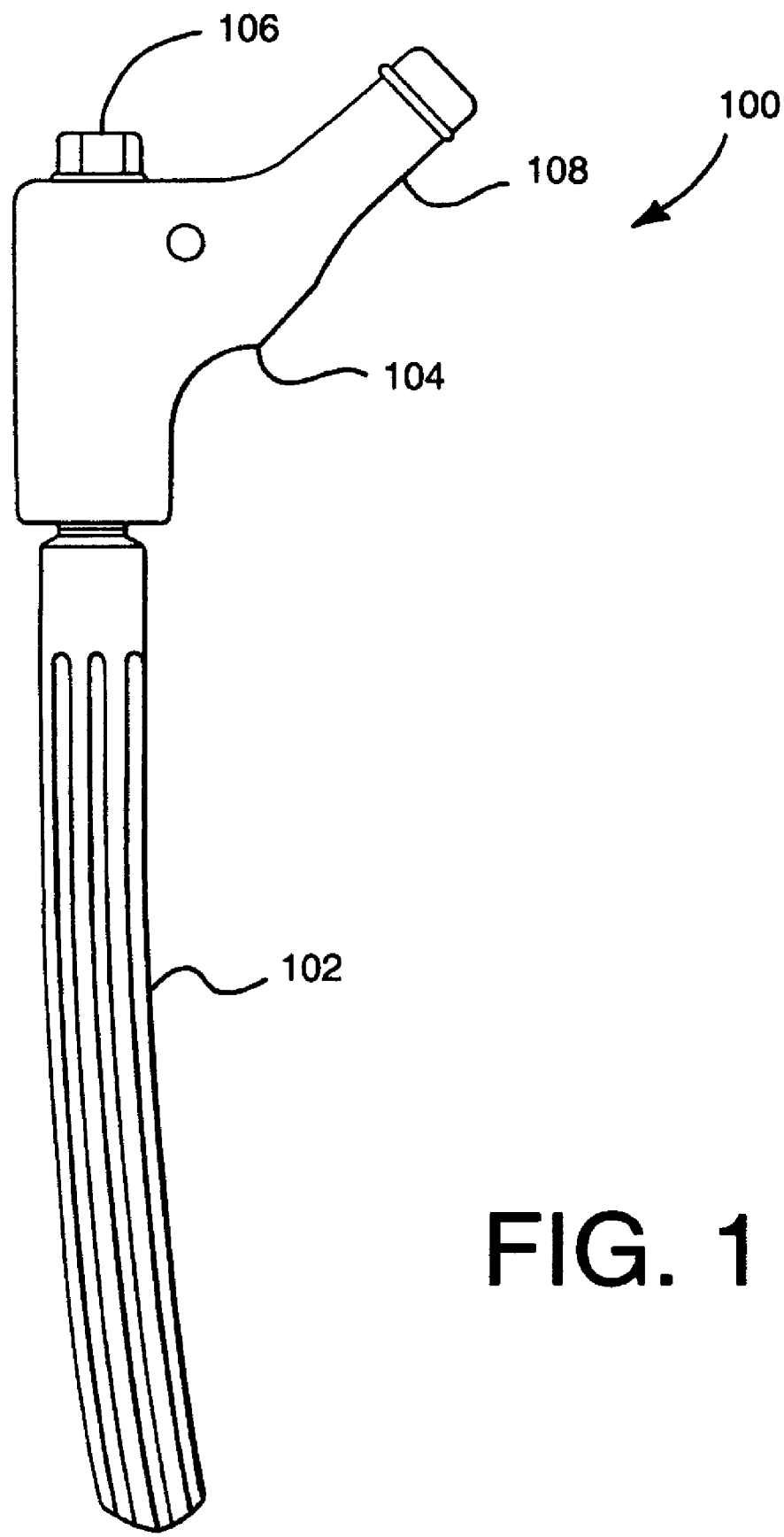
FIG. 1 depicts a side plan view of a modular trial assembly in accordance with principles of the present invention.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Referring now to FIG. 1, there is shown a modular trial assembly 100 according to one embodiment of the invention, including a distal trial stem 102, a proximal trial body 104 and a locking nut 106. The proximal trial body 104 includes a neck segment 108. The distal trial stem 102 is separate from the proximal trial body 104. In an alternative embodiment, the neck segment 108 is also separate from the proximal trial body 104. The modular trial assembly 100 can be made of stainless steel or another suitable material such as titanium, cobalt, etc.

Figure 2:
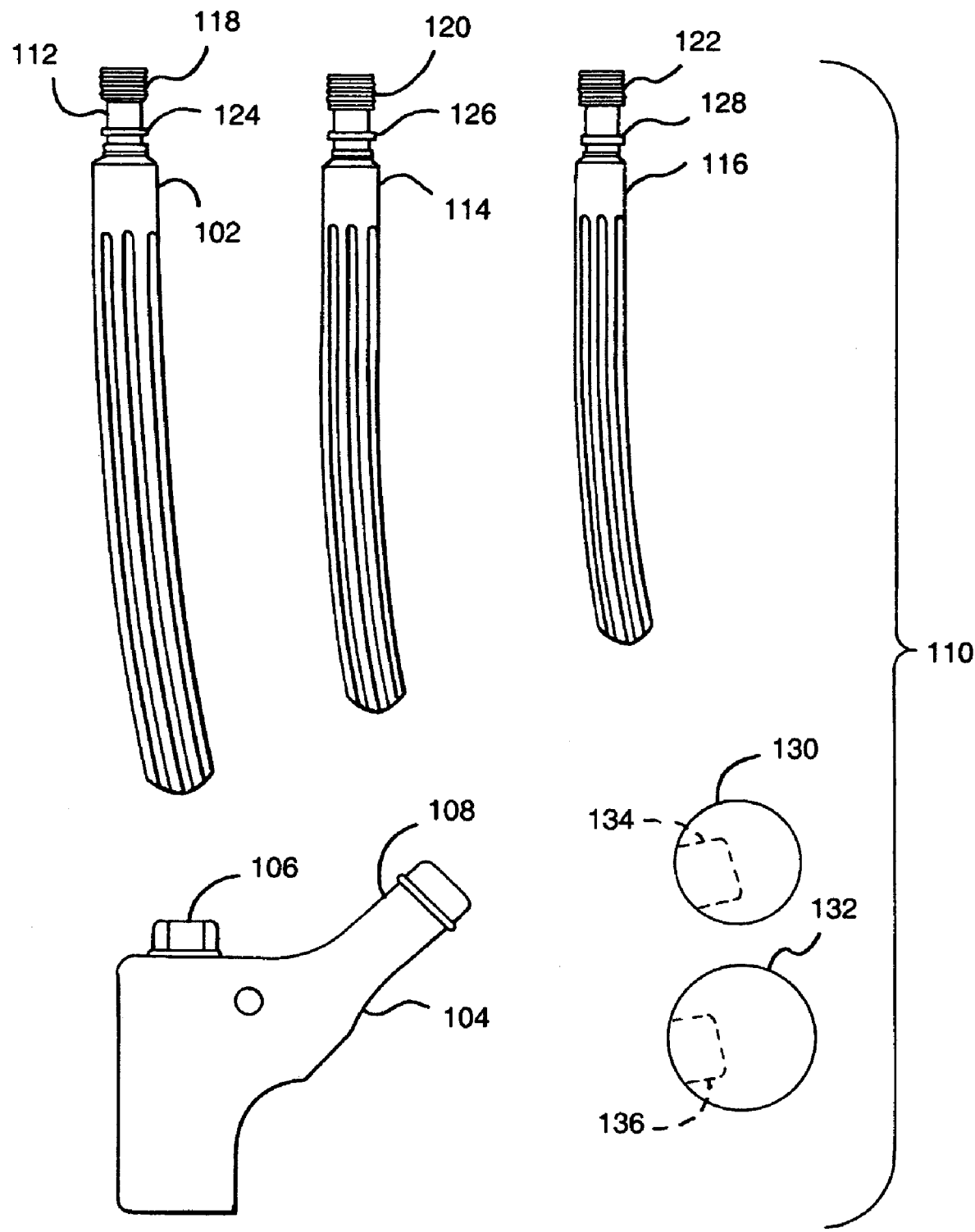
FIG. 2 depicts a side plan view of the components of an exemplary modular trial kit in accordance with principles of the present invention.

In the embodiment of FIG. 1, the proximal trial body 104 is shown in use with the distal trial stem 102. The proximal trial body 104 may also be used with other trial components. As shown in FIG. 2, a trial system kit 110 can include multiple sizes of components. In this embodiment, the trial system kit 110 includes the proximal trial body 104 and distal trial stems 102, 114 and 116 which have different sizes and/or shapes. Each of the distal trial stems 102, 114 and 116 include an identically threaded upper portion 118, 120 and 122, respectively and identical flanges 124, 126 and 128. A neck such as the neck 112 extends between each of the threaded upper portions 118, 120 and 122 and flanges 124, 126 and 128. Additionally, the trial system kit 110 includes femoral heads 130 and 132 which are of different sizes. The femoral heads 130 and 132 include internal bores 134 and 136, respectively, which are sized to receive the neck segment 108.

In kits wherein a separate neck segment is provided, necks of various lengths may also be included. Additionally, a variety of proximal trial bodies may be provided. The proximal trial bodies may have different outer diametric and/or geometric sizes, various vertical heights and various lateral offsets. Further embodiments include proximal trial bodies with geometric features such as calcar bodies, metaphyseal filling and conical shapes. Moreover, the kit may include reamers, broaches and implants, each of which include threaded upper portions and each of which may or may not include a flange. Thus, different sizes and shapes of components can be mixed and matched with one another to produce a modular trial assembly that matches the size and shape of a patient's joint anatomy.

Referring now to FIG. 3, the proximal trial body 104 is shown in cross-section with various components removed for clarity. The proximal trial body 104 includes an internal bore 138. A cavity 140 extends outwardly from the internal bore 138. The internal bore 138 further includes a main bore portion 142 which is separated from the cavity 140 by a lip 144 which protrudes into the internal bore 138.

The nut 106, shown in FIG. 4, includes a main body 146 which is sized to be received within the main bore portion 142. The nut 106 includes one end portion 148 which is configured to be rotated by a tool such as a wrench. A bore 150 (see FIG. 5) extends from the end portion 148 to another end portion 152 where the bore 148 expands to form a collet 154. The collet 154 includes an upper portion 156 and a bottom portion 158 separated by a wall 160. A plurality of cutouts 162 are located about the wall 160.

A threaded portion 164 is located within the bore 148. The threaded portion 154 is configured to threadedly engage the threaded portions 118, 120 and 122 of the distal trial stems 102, 114 and 116. The threaded portion 164 may be further configured to threadingly engage one or more of an implant, a broach and a reamer. In this embodiment, the upper portion 156 and the bottom portion 158 of the collet 154 are curvilinear and the entire collet 154 is formed from series 300 stainless steel, preferably with a wall thickness of between about $15/1000$ of an inch and $60/1000$ of an inch.

When the trial proximal body 104 is assembled as shown in FIG. 5, the main body 146 of the nut 106 is positioned within the main bore portion 142. The bottom portion 158 of the collet 154 is located within the main bore portion 142 above the lip 144. A spring washer 166 is located between the bottom portion 158 of the collet 154 and the lip 144. The bottom portion 158 of the collet 154 is sized such that the bottom portion 158 of the collet 154 cannot pass beyond the lip 143. The nut 106 is maintained within the bore 138 by a weld 168. Additionally, a spring 170 is located within the cavity 140.

Figure 8:
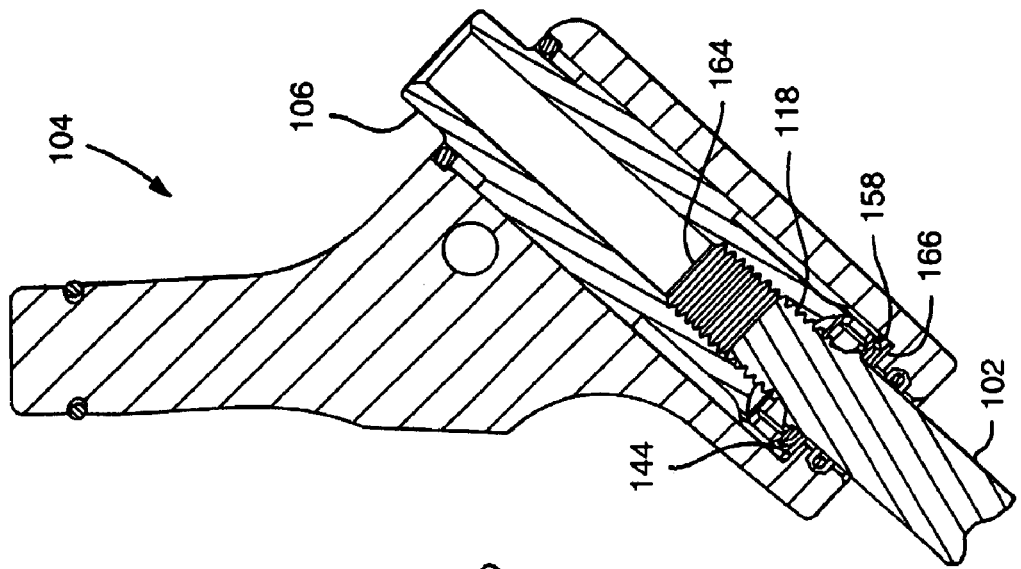
FIGS. 6-8 depict a distal trial implant being inserted and angularly locked within the proximal trial body of FIG. 1.
Figure 7:
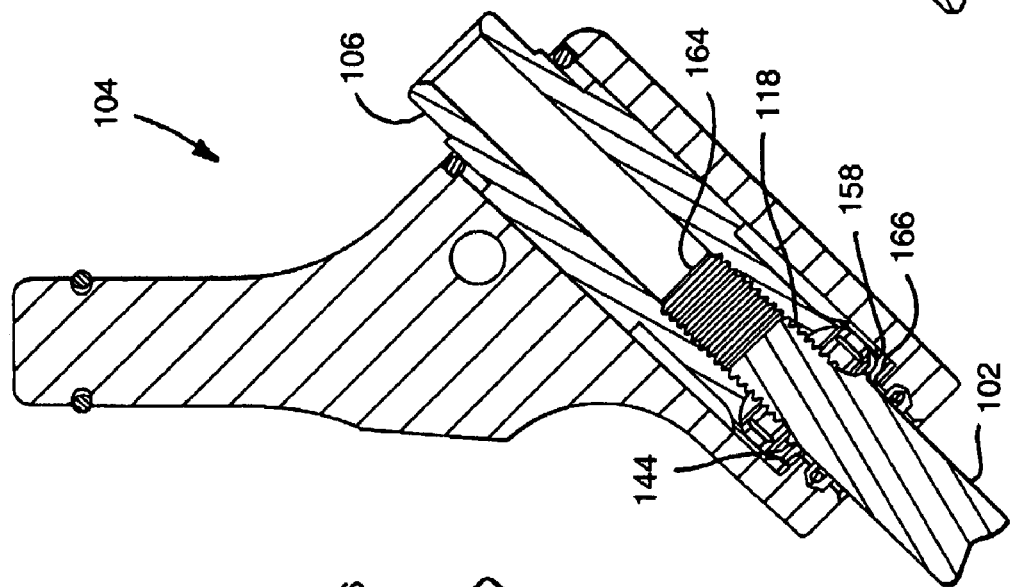
Figure 6:
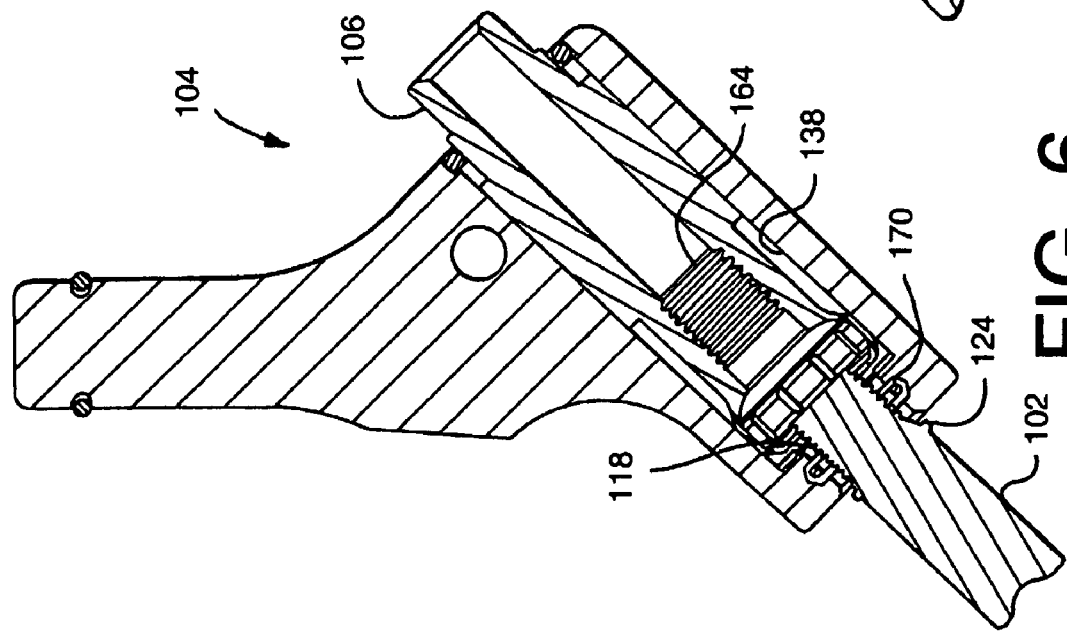

Referring now to FIGS. 6-8, an exemplary operation of the proximal trial mount 104 is explained. Initially, a patient is prepared for surgery and an incision is made to access the bone which is to receive a distal implant. Once the medullary canal of the bone is accessed, the bone is reamed in preparation of receiving the distal implant. A distal member is then positioned within the medullary canal. In various embodiments, a reamer, a broach or an implant is configured to be used as a distal trial stem.

Once the desired distal member is positioned within the medullary canal, which in this example is the distal trial stem 102, the proximal trial body 104 is placed on the distal member. Specifically, the distal trial stem 102 is received into the internal bore 138. As the threaded upper portion 118 passes into the main bore portion 142, the flange 124 contacts the spring 170, forcing the spring 170 outwardly from the longitudinal axis of the bore 138 into the cavity 140. When the spring 170 is forced into the cavity 140, the flange 124 is allowed to pass beyond the spring 170. As the flange 124 passes the spring 170, the spring 170 resiliently returns to its original shape, thus trapping the flange 124 within the bore 138 until such time as sufficient force is applied to the distal trial stem 102 to force the flange 124 past the spring 170.

In this condition, the distal trial stem 102 is loosely engaged with the proximal trial body 104. The proximal trial body 104 may then be rotated with respect to the distal trial stem 102 to the desired configuration. Alternatively, the locking nut 106 may be rotated in the clockwise direction. The rotation of the locking nut 106 in the clockwise direction causes the threaded portion 164 of the locking nut 106 to engage the threaded upper portion 118 of the distal trial stem 102.

Continued rotation of the nut 106 in the clockwise direction pulls the locking nut 106 downwardly toward the distal trial stem 102. As the nut 106 travels downwardly, the bottom portion 158 of the collet 154 compresses the spring washer 166 against the lip 144. Once the spring washer 166 is sufficiently compressed, movement of the bottom portion 158 of the collet 154 is restricted. The material, wall thickness and the cutouts 162 of the collet 154 are selected such that further rotation of the locking nut 106 causes elastic deformation of the collet 154. Specifically, the upper portion 156 of the collet 154 is forced toward the bottom portion 158 causing the wall 160 of the collet 154 to move outwardly from the longitudinal axis of the distal trial stem 102.

The outwardly movement of the wall 160 forces the wall 160 against the wall of the internal bore 138 as shown in FIG. 5. The height of the wall 160 provides a large contact area between the collet 154 and the internal bore 138. Accordingly, a strong frictional lock is provided between the proximal trial body 104 and the distal trial stem 102 through the collet 154 and the nut 106.

Once the distal trial stem 102 and the proximal trial body 104 are angularly locked, and a femoral head, such as femoral head 130, is placed onto the neck segment 108, the surgeon may perform a trial reduction to assess the desirability of the configuration of the modular trial assembly 100. Once the assessment is completed, the proximal trial body 104 is initially loosened by rotating the nut 106 in the counter-clockwise direction. The counter-clockwise rotation causes the nut 106 to move upwardly, away from the rim 144. This allows the collet 154 to elastically decompress. The decompression of the collet 154 continues until the nut 106 is no longer compressing the spring washer 166, thereby removing the angular lock between the distal trial stem 102 and the proximal trial body 104.

If desired, the angle between the distal trial stem 102 and the proximal trial body 104 may be modified. For example, one or more trial components may be replaced, or the angle between the distal trial stem 102 and the proximal trial body 104 may be altered and a subsequent trial reduction performed.

When the configuration provided by the modular trial assembly 100 is determined to be optimal, the modular trial assembly 100 may be removed and replaced with permanent implants mimicking the configuration of the modular trial assembly 100. This is accomplished by continued rotation of the nut 106 in the counterclockwise direction until the upper threaded portion 118 of the distal trial stem 102 is no longer engaged with the threaded portion 164. The proximal trial body 104 is then removed from the distal trial stem 102 by moving the proximal trial body 104 upwardly until the flange 124 contacts the spring 170 forcing the spring 170 into the cavity 140. The proximal trial body 104 is then separated from the distal trial stem 102.

Figure 9:
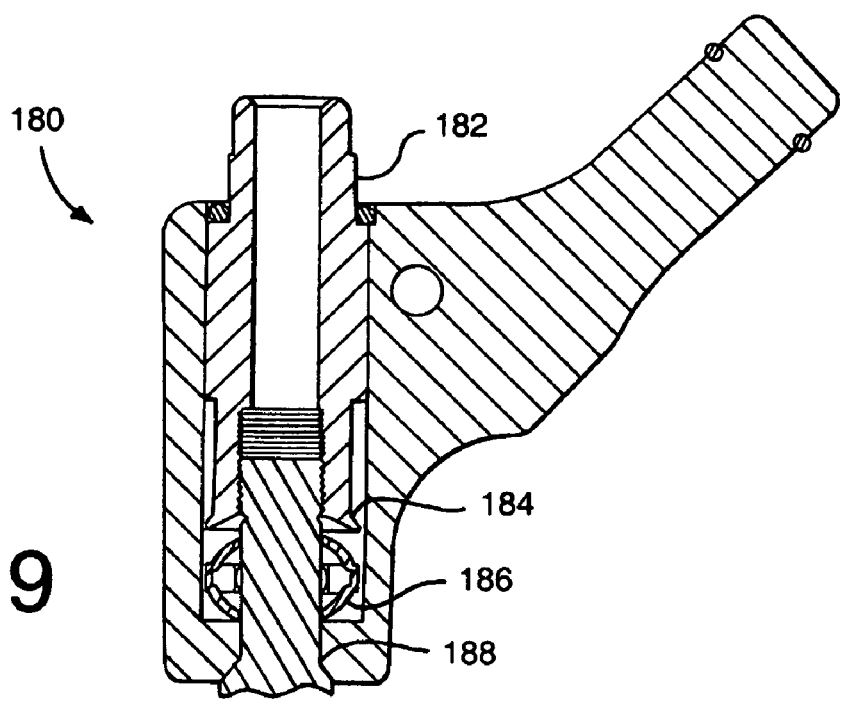
FIG. 9 depicts an alternative embodiment of a proximal trial body with a separately formed nut and collet used to angularly lock the proximal trial body with a distal implant in accordance with principles of the present invention.

Those of ordinary skill in the art will appreciate that a number of variations of the invention are possible. By way of example, FIG. 9 shows an alternative proximal trial body 180. The proximal trial body 180 is shown with a nut 182 that includes a lower portion 184 that is configured to engage a collet 186 in order to angularly lock the proximal trial body 180 with a distal implant 188.

Figure 10:
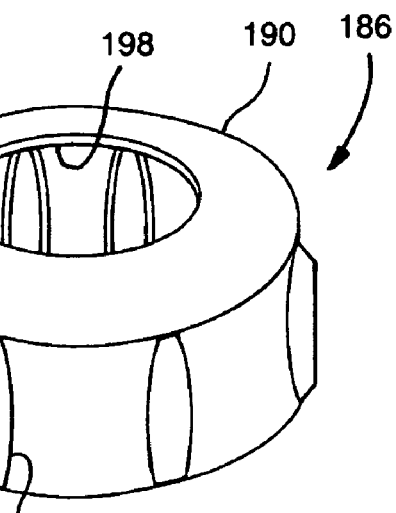
FIG. 10 depicts a perspective view of the collet of FIG. 9 showing the walls and ribs of the collet.

As shown in FIG. 10, the collet 186 includes an upper portion 190 and a bottom portion 192 separated by a wall 194. A plurality of ribs 196 are located about the wall 194. The upper portion 190 and the bottom portion 192 define openings 198 and 200 (see FIG. 11), respectively. The upper portion 190 is configured to be generally complementary with the lower portion 184 of the nut 182. Additionally, the openings 198 and 200 are configured to be just slightly larger in diameter than the portion of the distal implant 188 that extends through the collet 186 as shown in FIG. 9.

Figure 11:
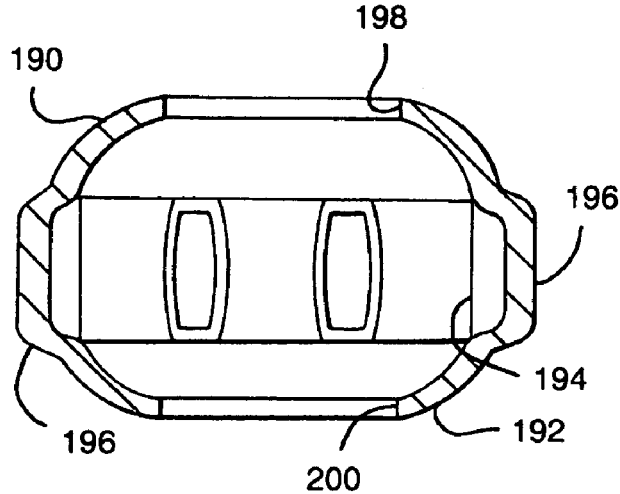
FIG. 11 depicts a side cross-section view of the collet of FIG. 9.

The embodiment shown in FIGS. 9-11 is operated in much the same manner as the modular trial assembly 100 of FIG. 1. One difference is that as the collet 186 is collapsed, the ribs 196 provide the binding contact with the proximal trial body 180. Additionally, the resilient deformation of the collet 186 causes the openings 198 and 200 to bind with the distal implant 188 providing a frictional lock in addition to the frictional lock between the nut 182 and the distal implant 188. Accordingly, a strong angular lock between the distal implant 188 and the proximal trial body 180 is achieved.

Figure 12:
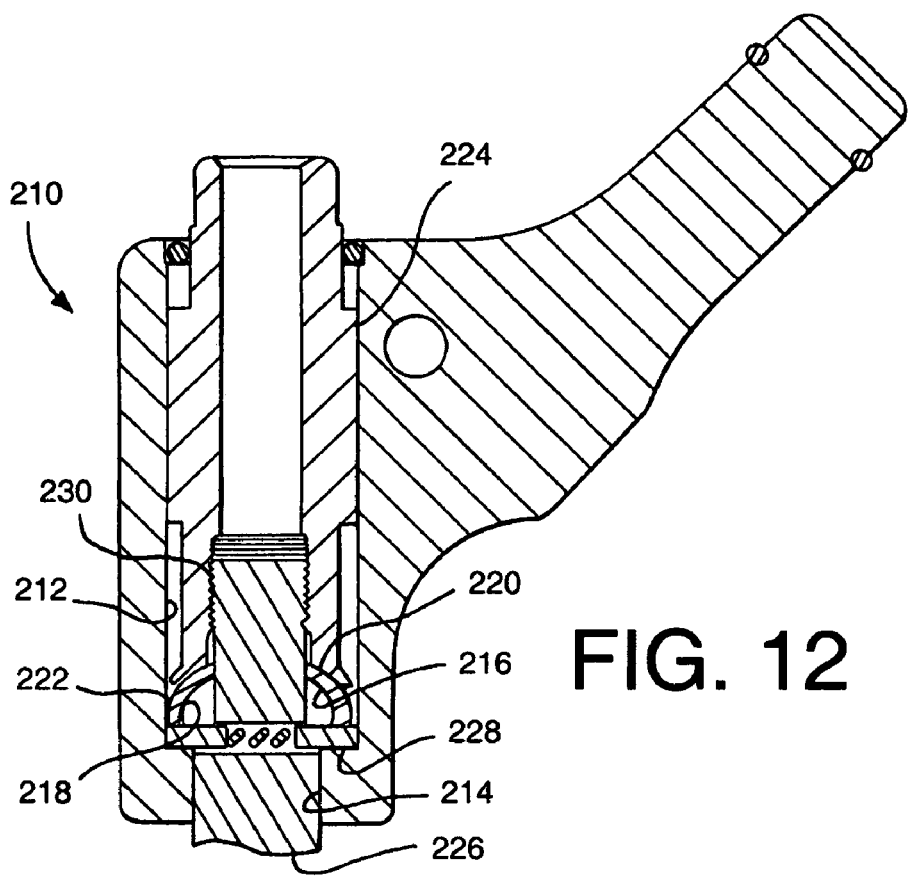
FIG. 12 depicts an alternative embodiment of a proximal trial body with a separately formed nut and collet used to angularly lock the proximal trial body with a broach that includes an expandable flange in accordance with principles of the present invention.

A further alternative embodiment is shown in FIG. 12. The proximal trial body 210 includes a main bore portion 212 and a lower bore portion 214. A collet 216 is located within the main bore portion 212. The collet 216 includes a bottom portion 218, a top portion 220 and an outer wall 222. A nut 224 is also located within the main bore portion 212. The broach 226 which is used with the proximal trial body 210 includes an expandable flange 228 and a threaded portion 230.

The, the flange 228 is configured to expand within the main bore portion 212 of the proximal trial body 210. Thus, when angularly locking the proximal trial body 210 and the broach 226, the collet 216 is compressed between the nut 224 and the expandable flange 228. Another variation in the embodiment of FIG. 12 is that the bottom portion 218 of the collet 216 is not symmetrical with the top portion 220. This is because the bottom portion 218 is configured to extend only partially over the lower bore portion 214 while the outer wall 222 of the collet 216 extends outwardly of the lower bore portion 214 when the collet 210 is not compressed. Thus, the outer wall 222 prevents the collet 216 from falling through the lower bore portion 214 when the broach 226 is not inserted within the proximal trial body 210. Moreover, the partial extension of the bottom portion 218 over the lower bore portion 214 allows the threaded portion 230 of the broach 226 to pass through the collet 216 while ensuring that the flange 228 entraps the collet 216 between the flange 228 and the nut 224 when the flange 228 is inserted into the main bore portion 212.

Additionally, in this embodiment, the collet 216 does not have ribs. The outer wall 222 of the collet 216, however, is slightly curved in an outwardly direction when the collet 216 is in an uncompressed state. Thus, as the collet 216 is elastically deformed, the surface area of the wall 222 that contacts the wall of the main bore portion 212 increases.

Figure 13:
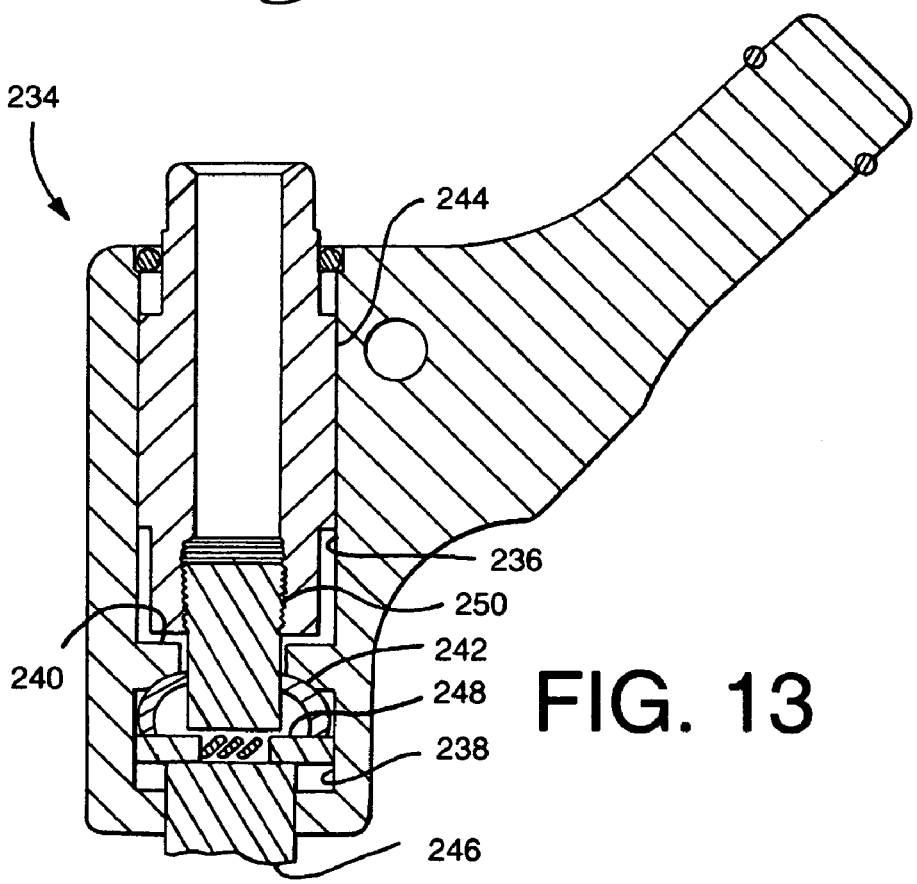
FIG. 13 depicts an alternative embodiment of a proximal trial body with a separately formed nut and collet used to angularly lock the proximal trial body with a reamer that includes an expandable flange in accordance with principles of the present invention.

Yet another alternative embodiment is shown in FIG. 13. The proximal trial body 234 includes a main bore portion 236 and a lower bore portion 238 separated by a lip 240. A collet 242 is located within the lower bore portion 238. The collet 242 is similar to the collet 216. A nut 244 is also located within the main bore portion 236. The reamer 246 which is used with the proximal trial body 234 includes an expandable flange 248 and a threaded portion 250.

The embodiment of FIG. 13 works similarly to the embodiment of FIG. 12. The main difference is that the collet 242 is compressed between the flange 248 and the lip 240. Thus, the nut 244 compresses the collet 242 indirectly.

While the present invention has been illustrated by the description of exemplary processes and system components, and while the various processes and components have been described in considerable detail, applicant does not intend to restrict or in any way limit the scope of the appended claims to such detail. Additional advantages and modifications will also readily appear to those ordinarily skilled in the art. The invention in its broadest aspects is therefore not limited to the specific details, implementations, or illustrative examples shown and described. Accordingly, departures may be made from such details without departing from the spirit or scope of applicant's general inventive concept. By way of example, but not of limitation, the system described herein may be applied to other bones and joints besides the hip. Such bones may include tibial and humerus bones.

We claim:

1. A femoral hip implant kit comprising:
   at least one distal implant;
   a plurality of femoral heads, each of the plurality of femoral heads having a diameter different from the diameter of the other of the plurality of femoral heads;
   a proximal trial housing defining a first opening, a second opening, and a bore extending therebetween, the bore (i) defining an axis, (ii) defining a bore wall interposed between the first opening and the second opening, and (iii) configured to receive a portion of the at least one distal implant through the first opening;
   a collet positioned within the bore, the collet including an outer wall portion, an upper portion and a bottom portion; and
   a collapsing member configured to (i) engage the portion of the distal implant, and (ii) move in relation to said collet within said bore along the axis,
   wherein movement of the collapsing member in relation to the collet within the bore along the axis when movement of the bottom portion along the axis is constrained causes movement of the upper portion of the collet towards the bottom portion of the collet along the axis,
   wherein movement of the upper portion of the collet towards the bottom portion of the collet along the axis causes movement of the outer wall portion of the collet in a direction generally perpendicular to the axis so as to force the outer wall portion into contact with the bore wall, and
   wherein the collapsing member comprises: (i) a main body portion configured to fit within the bore; (ii) a threaded internal bore within the main body for threadingly receiving the portion of the distal implant; and (iii) a head portion for receiving torque.

2. The femoral hip implant kit of claim 1, wherein:
   an upper portion of the collet is integrally formed with the collapsing member, and
   said collapsing member is configured to move in relation to a lower portion of the collet.

3. The femoral hip implant kit of claim 1, wherein:
   a protuberance is located within the bore; and
   the collet is located between the collapsing member and the protuberance.

4. The femoral hip implant kit of claim 1, wherein:
   the distal implant is configured to be axially locked within the bore; and
   the collet is located between the collapsing member and the distal implant.

5. The femoral hip implant kit of claim 1, wherein:
   said outer wall portion of the collet includes a plurality of contact structures spaced apart from each other,
   said collet defines a plurality of cutouts spaced apart from each other, and
   each of said plurality of cutouts is interposed between a first contact structure and a second contact structure of an adjacent pair of contact structures of said plurality of contact structures.

6. The femoral hip implant kit of claim 5, wherein all of said plurality of contact structures are advanced in the direction generally perpendicular to the axis and into contact with the bore wall in response to movement of the upper portion of the collet towards the bottom portion of the collet along the axis.

7. A femoral hip implant kit comprising:
   at least one distal implant;
   a plurality of femoral heads, each of the plurality of femoral heads having a diameter different from the diameter of the other of the plurality of femoral heads;
   a proximal trial housing defining a first opening, a second opening, and a bore extending therebetween, the bore (i) defining an axis, (ii) defining a bore wall interposed between the first opening and the second opening, and (iii) configured to receive a portion of the at least one distal implant through the first opening;
   a collet positioned within the bore, the collet including an outer wall portion, an upper portion and a bottom portion; and
   a collapsing member configured to (i) engage the portion of the distal implant, and (ii) move in relation to said collet within said bore along the axis,
   wherein movement of the collapsing member in relation to the collet within the bore along the axis when movement of the bottom portion along the axis is constrained causes movement of the upper portion of the collet towards the bottom portion of the collet along the axis,
   wherein movement of the upper portion of the collet towards the bottom portion of the collet along the axis causes movement of the outer wall portion of the collet in a direction generally perpendicular to the axis so as to force the outer wall portion into contact with the bore wall, and
   wherein: (i) a protuberance is located within the bore; and (ii) the collet is located between the distal implant and the protuberance.

8. A method of trialing an implant comprising:
   providing a bore within a proximal trial housing;
   providing a collet within the bore;
   receiving a portion of a distal implant within the bore;
   engaging the portion of the distal implant within the proximal trial housing;
   moving an upper portion of the collet closer to a bottom portion of the collet along an axis;
   forcing an outer wall portion of the collet in a direction generally perpendicular to the axis in response to the moving step; and
   contacting a wall defined by the bore with the outer wall portion of the collet in response to the forcing step such that the distal implant is angularly locked to the proximal trial housing,
   wherein the moving step comprises collapsing the collet between a locking nut and the proximal trial housing.

9. The method of claim 8, wherein:
   said outer wall portion of the collet includes a plurality of contact structures spaced apart from each other,
   said collet defines a plurality of cutouts spaced apart from each other, and
   each of said plurality of cutouts is interposed between a first contact structure and a second contact structure of an adjacent pair of contact structures of said plurality of contact structures.

10. The method of claim 9, wherein said contacting step includes the step of advancing all of said plurality of contact structures in the direction generally perpendicular to the axis and into contact with the bore wall in response to the forcing step.

11. A method of trialing an implant comprising:
    providing a bore within a proximal trial housing;
    providing a collet within the bore;
    receiving a portion of a distal implant within the bore;

engaging the portion of the distal implant within the proximal trial housing;

moving an upper portion of the collet closer to a bottom portion of the collet along an axis;

forcing an outer wall portion of the collet in a direction generally perpendicular to the axis in response to the moving step; and contacting a wall defined by the bore with the outer wall portion of the collet in response to the forcing step such that the distal implant is angularly locked to the proximal trial housing, wherein the moving step comprises collapsing the collet between a locking nut and the distal implant.

* * * * *